United States Patent

Harrod et al.

Patent Number: 5,955,626
Date of Patent: Sep. 21, 1999

[54] PROCESS OF PURIFYING DIHYDROCARBYLCHLOROTHIOPHOSPHATES

[75] Inventors: William B. Harrod, Baton Rouge, La.; Thomas J. Callender, Magnolia, Ark.; David Edward Raposa, Minden, La.

[73] Assignee: Albemarle Corporation, Richmond, Va.

[21] Appl. No.: 09/248,941

[22] Filed: Feb. 12, 1999

[51] Int. Cl.⁶ .................................................. C07F 9/14
[52] U.S. Cl. .......................................... 558/148; 558/202
[58] Field of Search ............................................. 558/148

[56] References Cited

U.S. PATENT DOCUMENTS

| | | |
|---|---|---|
| 3,089,890 | 5/1963 | Chupp et al. . |
| 3,098,866 | 7/1963 | Divine ..................................... 558/148 |
| 4,247,490 | 1/1981 | Bergeron et al. ...................... 558/148 |
| 4,354,983 | 10/1982 | Roszinski et al. ..................... 558/148 |

*Primary Examiner*—Michael G. Ambrose
*Attorney, Agent, or Firm*—Philip M. Pippenger

[57] ABSTRACT

Crude dihydrocarbylchlorothiophosphate product contaminated with dihydrocarbylpolysulfide and/or dihydrocarbylchlorophosphate is upgraded by treating the crude product with chlorine followed by an aqueous solution of reducing agent, separating an aqueous phase from the organic, then drying to obtain the resultant product.

27 Claims, 1 Drawing Sheet

PROCESS OF PURIFYING DIHYDROCARBYLCHLOROTHIOPHOSPHATES

BACKGROUND

As noted in U.S. Pat. No. 3,089,890 to Chapp and Newallis, dihydrocarbylchlorothiophosphates (a.k.a. O,O-dihydrocarbylphosphorochloridothioates), such as diethylchlorothiophosphate are of considerable value as intermediates in the manufacture of pesticidal agents, and can also be used for manufacture of other types useful products.

In the production of dihydrocarbylchlorothiophosphates, small amounts of an undesirable dihydrocarbylpolysulfide coproduct, typically a dihydrocarbyltrisulfide, tend to be formed. Even amounts of less than 0.5 wt % in the dihydrocarbylchlorothiophosphate reaction product is of concern because of its highly disagreeable, persistent odor. Usually still another undesirable coproduct is formed during the production of the dihydrocarbylchlorothiophosphate. This impurity is the oxygen analog of the desired product, i.e., the corresponding dihydrocarbylchlorophosphate, the separation of which is addressed in the foregoing Chapp and Newallis patent. Unfortunately, although this latter impurity can be effectively removed to satisfactorily low levels by the aqueous washing and extraction procedure described in that patent, the Chapp and Newallis procedure described in the patent is incapable of removing the offensive dihydrocarbyltrisulfide impurity to the low levels desired in the final product.

A need thus exists for an effective, commercially feasible way of upgrading the quality of dihydrocarbylchlorothiophosphates by removing therefrom the dihydrocarbylpolysulfide impurities, notably the dihydrocarbyltrisulfide, if not completely, then at least to acceptably low levels. At the same time it would highly advantageous if the procedure would have the capability of concurrently removing the dihydrocarbylchlorophosphate impurity, when copresent, to satisfactorily low levels. It would also be desirable to provide a new, efficient way of removing dihydrocarbylchlorophosphate from crude dihydrocarbylchlorothiophosphates, or at least reducing the dihydrocarbylchlorophosphate impurity content of crude dihydrocarbylchlorothiophosphates, in any situation where no dihydrocarbylpolysulfide impurity is copresent.

In commonly owned copending application Ser. No. 09/249,361, filed Feb. 12, 1999, a process is described in which the above impurities in a crude dihydrocarbylchlorothiophosphate product are removed, if not completely, then at least to acceptably low levels. This is accomplished in that process by use of an aqueous hypochlorite solution as a treating agent for the crude dihydrocarbylchlorothiophosphate product. The application notes that it appears that in situ release of chlorine probably occurs and plays a role in the purification reactions that take place on contacting an aqueous hypochlorite solution with the crude product contaminated with such impurities. While the process described in that application Ls effective in reducing the content of these impurities, loss of some of the desired product can occur. Also the process requires more raw materials, and generates more aqueous waste than desired.

BRIEF SUMMARY OF THE INVENTION

Process technology has now been discovered which is capable of effectively and efficiently reducing the content of the foregoing impurities in a crude dihydrocarbylchlorothiophosphate product. Moreover, this invention makes it possible to achieve these objectives without imposing any significant reduction in the yield of the dihydrocarbylchlorothiophosphate product formed in the production process. In addition, the process requires less raw materials and if properly conducted, results in generation of less aqueous waste than the above processes.

Pursuant to this invention elemental chlorine is introduced into the crude product, then the chlorine-treated product is contacted with an aqueous alkaline solution, preferably a solution of a reducing agent, to quench any residual chlorine and form an aqueous phase which is separated from the resultant treated product. Optionally, one or more aqueous extractions of the treated product can be carried out before or after the phase separation. The process of this invention effectively removes at least a significant portion of the dihydrocarbylpolysulfide impurity and in addition, also effectively reduces the content of dihydrocarbylchlorophosphate impurity if present in the crude product. Likewise, the process of this invention can be effectively used to reduce the content of dihydrocarbylchlorophosphate impurity in any situation where the crude dihydrocarbylchlorothiophosphate happens to be free of dihydrocarbylpolysulfide impurity.

Another feature of this invention is that it can be, and preferably is, conducted as a continuous process, although it can be performed as a batch process or as a semi-continuous process, if desired.

Preferably, the initial crude product subjected to the process of this invention is a distilled crude product. However this is not a requirement as benefits can be realized by conducting the process with non-distilled reaction product mixtures.

The above and other embodiments of this invention will be still further apparent from the ensuing description and appended claims.

FURTHER DETAILED DESCRIPTION

Figure 1:
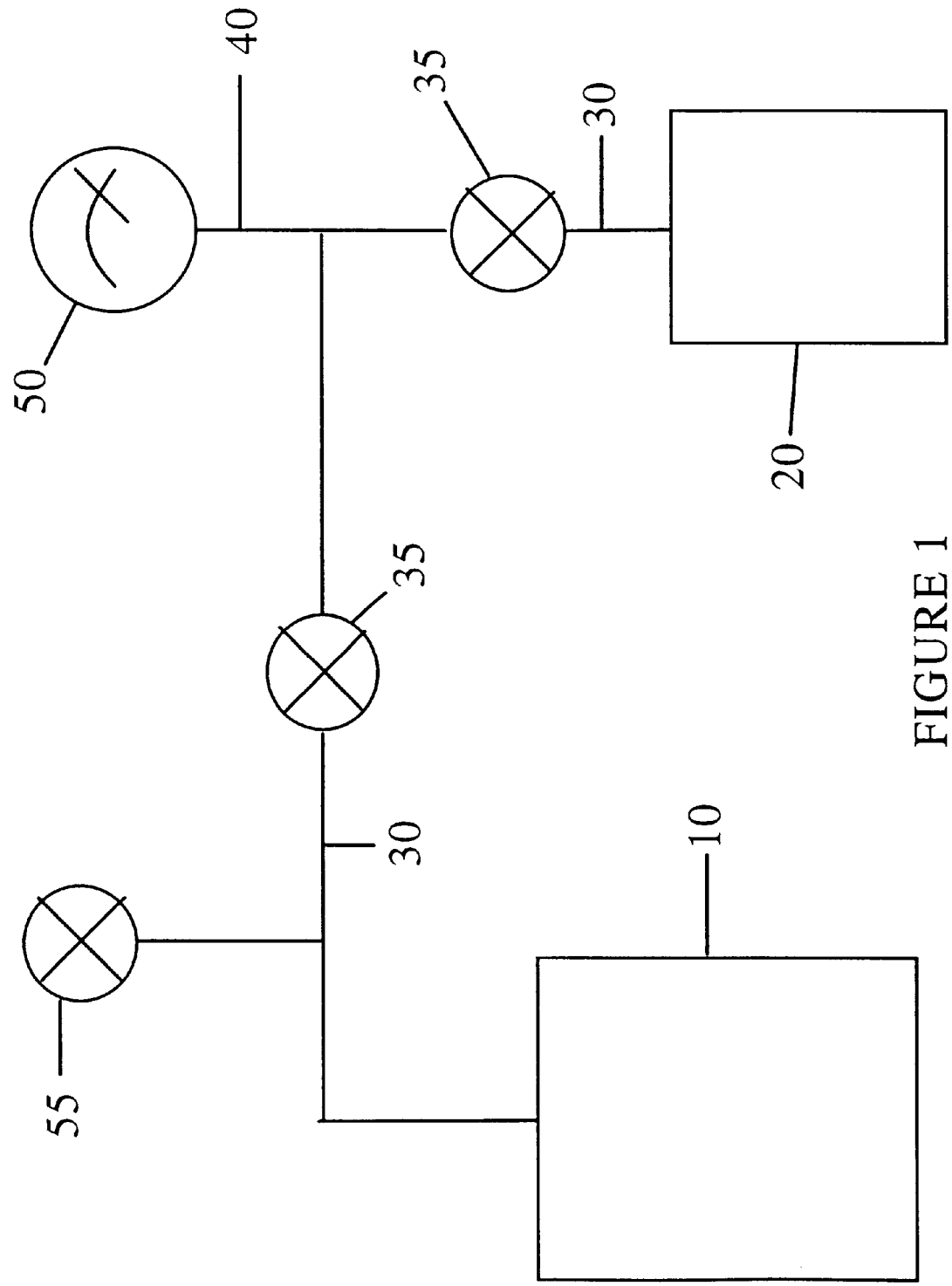
FIG. 1 schematically depicts the apparatus referred to in Example 1 hereinafter.

Dihydrocarbylchlorothiophosphates which can be purified pursuant to this invention are adequately described in U.S. Pat. No. 3,089,890, supra. Thus the hydrocarbyl groups are free of non-benzenoid unsaturation, and typically each such group (e.g., alkyl, cycloalkyl, cycloalkylalkyl, aryl, alkylaryl, aralkyl, etc.) contains 1 to about 8 carbon atoms. A few examples of such compounds include dimethylchlorothiophosphate, dipropylchlorothiophosphate, diisopropylchlorothiophosphate, dibutylchlorothiophosphate, diisobutylchlorothiophosphate, dipentylchlorothiophosphate, dihexylchlorothiophosphate, dioctylchlorothiophosphate, dicyclopentylchlorothiophosphate, dicyclohexylchlorothiophosphate, dicyclopropylcarbinylchlorothiophosphate, diphenylchlorothiophosphate, ditolylchlorothiophosphate, dibenzylchlorothiophosphate, and their analogs and homologs containing up to about 8 carbon atoms in each hydrocarbyl group. Because of its present substantial industrial importance, the process of this invention is preferably applied to the purification of diethylchlorothiophosphate. The only requirement is that the crude dihydrocarbylchlorothiophosphate subjected to the process contains (i) at least one dihydrocarbylpolysulfide impurity or (ii) at least one dihydrocarbylchlorophosphate impurity, or (iii) a combination of (i) and (ii). The process of this invention is preferably applied to crude dihydrocarbylchlorothiophosphates that are contaminated with at least one dihydrocarbylpolysulfide impurity or with the combination of at least one dihydrocarbylpolysulfide impurity and at least one dihydrocarbylchlorophosphate impurity. Conventional amounts of still other conventional impurities do not have any material adverse effect upon the efficacy of the purification process of this invention. If however an impurity happens to be present that would have a material adverse effect upon the efficacy of the purification process of this invention, such impurity should be removed before using the process of this invention.

Thus although the particular impurities with which this invention is concerned are either or both of dihydrocarbylpolysulfides and dihydrocarbylchlorophosphates, the crude dihydrocarbylchlorothiophosphate products subjected to the process of this invention usually will contain one or more other impurities, and the amounts of these may or may not be reduced in the practice of this invention.

The process of this invention thus can be applied to crude dihydrocarbylchlorothiophosphate product produced by any process that results in the presence in the product (preferably a distilled product) of at least one dihydrocarbylpolysulfide impurity and/or at least one dihydrocarbylchlorophosphate impurity. The amount of such impurity or impurities in the crude dihydrocarbylchlorothiophosphate product is not critical as the purification process of this invention has the capability of removing any quantity typically found in the product. Typically the amounts of either or both of these two types of impurities (i.e., dihydrocarbylpolysulfide and dihydrocarbylchlorophosphate) will not exceed about 2 wt % of the weight of the pure dihydrocarbylchlorothiophosphate, and in most cases will be much lower than 2 wt %.

The mechanism by which the dihydrocarbylpolysulfide impurity is formed is not known. However, without being bound by theory, a possible explanation of the formation of such impurity may involve in whole or in part a reaction such as:

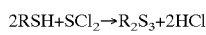

$$2RSH + SCl_2 \rightarrow R_2S_3 + 2HCl$$

At least in the case of diethylchlorothiophosphate production, the presence of ethyl mercaptan (EtSH) in distillation columns has been observed, presumably as a product of decomposition of nonvolatile organic thiophosphates located in the reactor.

It is preferred to employ the chlorine in gaseous form and to establish direct contact between the gaseous chlorine and the crude dihydrocarbylchlorothiophosphate product while the crude product is in a turbulent or agitated state. This ensures that the chlorine thoroughly contacts all portions of the crude liquid product. Thus the gaseous chlorine can be passed through a metering device and introduced in controlled amounts either continuously or in increments at suitably timed intervals (e.g., pulsated feeding) directly into an agitated body or a turbulent flowing stream of the crude dihydrocarbylchlorothiophosphate product. Use of countercurrent flows of the crude product and gaseous chlorine is another way of establishing intimate contact between the chlorine and impurities present in the crude product such as the dihydrocarbylpolysulfide impurity. Still another way of accomplishing such contact is to spray the crude dihydrocarbylchlorothiophosphate product into an atmosphere of gaseous chlorine. The reaction(s) that take place in the body or flow of the crude product to remove the dihydrocarbylpolysulfide such as diethyltrisulfide are extremely rapid even under ambient temperature conditions. Thus, any method of intimately contacting the crude product with gaseous chlorine can be used.

While not essential, it is preferred that the gaseous chlorine contact the crude product under anhydrous or substantially anhydrous conditions, the latter being anhydrous conditions that can be achieved in actual practice under practical, economically-feasible industrial plant conditions.

The gaseous chlorine can be mixed or diluted with one or more inert gases, such as nitrogen, argon, neon, krypton, or the like. Use of such diluted chlorine can facilitate controlled addition of small amounts of chlorine into the crude product.

In lieu of gaseous chlorine, it may be possible to use the chlorine in solution, either in water or in a suitable inert liquid carrier. However there would appear to be no particular advantage in so doing.

The amount of chlorine will of course be dependent upon the impurity content of the particular dihydrocarbylchlorothiophosphate product being treated. Normally an excess of chlorine relative to the impurity content is mixed with the crude product, the excess being an amount sufficient to reduce content of at least the dihydrocarbylpolysulfide present to at least an acceptable level. For example, in the case of diethylchlorothiophosphate it is possible to reduce the content of diethyltrisulfide to 0.05% or less, which percentage is a GC area percentage as determined with use of a thermal conductivity detector.

Since, as noted above, the reaction(s) between the chlorine and at least the dihydrocarbylpolysulfide impurity such as diethyltrisulfide is/are very rapid, the contact time between the chlorine and the crude product can be very short, e.g., in the range of a few seconds to a few minutes. With impurity levels typically found in distilled crude diethylchlorothiophosphate, the purification reactions are often completed in 10 minutes or less.

It will be appreciated, however, that even longer times than specified in the foregoing ranges can be used pursuant to this invention whenever deemed necessary or desirable under the particular circumstances involved.

The chlorine treatment can be conducted under any of a variety of temperature conditions. For example, the treatment can be conducted effectively at temperatures as low as about 15° C. Conversely, the treatment can be conducted at elevated temperatures as long as they are below the thermal decomposition temperature of the dihydrocarbylcholorothiophosphate being treated. Preferably however, the chlorine treatment is conducted under ambient temperature conditions as there is no need or reason to withdraw thermal energy from or apply thermal energy to the mixture being treated. While any temperature that is below the thermal decomposition temperature of the dihydrocarbylchlorothiophosphate being treated can be used, normally a temperature higher than about 80° C. would seem unnecessary.

It is possible to conduct the operation at superatmospheric pressure, if desired. However ordinarily the chlorine treatment is conducted at atmospheric pressure or at ambient elevated pressures that typically exist in a closed system.

It is to be understood and appreciated that the mechanism by which the chlorine purification reaction or reactions take place is unknown. One possible mechanism that may occur is that the chlorine may interact with one or more impurity components present in the crude product to form one or more intermediates which in turn interact with the unreacted impurity or impurities, such as a dihydrocarbylpolysulfide. For example, it is conceivable that the chlorine may immediately react in whole or in part with a dihydrocarbyl polysulfide impurity such as diethyltrisulfide to form an intermediate species such as Et2SS(Cl)SEt, which in turn may further react with remaining impurity content. On the other hand, reaction between chlorine and the dihydrocarbylpolysulfide might itself be directly responsible for the destruction of the polysulfide. For instance, it is possible that upon reaction of chlorine with diethyltrisulfide at low levels, sulfur of the polysulfide may be chlorinated selectively, with low levels of chloroethane being evolved upon excess halogenation, perhaps in accordance with the equation:

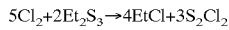

But whatever the actual mechanism(s) of the chlorine treatment, it works—the levels of dihydrocarbyl polysulfide impurities in the dihydrocarbylchlorothiophosphate can be effectively reduced by the process. Thus this invention is not to be limited by any theory or mechanism of reaction. If because of its concentration in the crude product, dihydrocarbylpolysulfide is the only impurity of concern, all that is necessary is to contact the crude dihydrocarbylchlorothiophosphate with the chlorine under the appropriate conditions described herein, and then contact the treated product with an aqueous alkaline solution to quench any residual chlorine and form an aqueous phase which is separated from the resultant treated product.

In situations where it is not necessary to decrease the amount of dihydrocarbylchlorophosphate impurity, if any, in the product, any of a variety of aqueous solutions containing a reducing agent can be used to quench the chlorine. For example, aqueous solutions of sodium sulfite or the like can be used.

In cases where it is desired to reduce the amount of both dihydrocarbylpolysulfide and dihydrocarbylchlorophosphate in the crude product, the product, after the chlorine treatment, is maintained in contact with an aqueous solution containing a reducing agent, for a sufficient period of time to ensure not only that any excess chlorine is quenched, but that the level of the dihydrocarbylchlorophosphate impurity has been reduced to a satisfactory or desired level. Typically, when purifying a distilled crude having typical amounts of these impurities (e.g., well below 2% of each) the chlorine-treated crude product is thoroughly mixed with the aqueous solution of reducing agent for a period in the range of about 5 to about 10 minutes as this will normally ensure that the level of the dihydrocarbylchlorophosphate impurity has been reduced to an acceptable level. However, pursuant to this invention, the contact time between the aqueous solution of reducing agent and the chlorine-treated crude product can be of any duration that may be required to achieve the desired reduction in the dihydrocarbylchlorophosphate impurity content.

Thus the product after treatment with the chlorine is treated or washed with an aqueous solution of a reducing agent, preferably an alkali metal sulfite or bisulfite (e.g., $Na_2SO_3$, $K_2SO_3$, $NaH_3S$, $KH_3O$, etc.) to quench any excess chlorine and to reduce the content of the dihydrocarbylchlorophosphate in the product. The aqueous initially alkaline solution of reducing agent can be of any suitable concentration but is typically made by dilution of fairly concentrated feedstock (15–50%) so as to reduce materials handling and the volume of aqueous waste produced. In many cases, after dilution, a 0.5 to 1.0 wt % aqueous solution will be used.

The chlorine quenching operation can be conducted at various temperatures, but typically it is conducted at one or more temperatures in the range of about 55 to about 75° C. For maximum efficiency the mixture of aqueous and organic phases should be well mixed to ensure intimate contact between the phases. Thereafter the product can be washed with water, if desired, but this is not necessary. Separation(s) of the aqueous and organic (product:) phases by decantation or any other suitable technique yields the purified dihydrocarbylchlorothiophosphate.

As indicated above, the purification process of this invention can be, and preferably is, conducted as a continuous process. One preferred form of such process comprises:

a) continuously feeding a crude dihydrocarbylchlorothiophosphate product contaminated with at least one dihydrocarbylpolysulfide and/or at least one dihydrocarbylchlorophosphate into a reaction zone while concurrently feeding chlorine into the reaction zone (either intermittently with short intervals of time between introductions or, preferably, continuously) such that the chlorine and the crude product come into intimate contact with each other allowing a reaction time of at least about 0.5–1.0 minutes;

b) concurrently withdrawing chlorine-contacted contents from the reaction zone at a volumetric rate substantially equivalent to the volumetric rate at which the feeds are being introduced into the reaction zone;

c) continuously feeding the contents withdrawn from the reaction zone into a quenching zone and mixing such contents therein with an aqueous solution of a reducing agent to at least quench any excess chlorine and extract from the dihydrocarbylchlorothiophosphate product water-soluble impurities present therein; and d) separating the resultant aqueous and organic (purified product) phases from each other.

The water or aqueous solution of a base, or aqueous solution of a reducing agent can be, but need not be, continuously fed into the quenching zone, and if it is, the contents can be continuously removed from the quenching zone. If desired, the purified product can be water washed (or again water washed), and then dried.

The water-soluble impurities in the chlorine-treated product comprise those formed during the chlorine-treatment and water-soluble impurities, if any, present ab initio. These are thus removed by use of water or an aqueous solution of a reducing agent as the feed to the quenching zone. Removal of solely the dihydrocarbylchlorophosphate impurity could be achieved without chlorine treatment per previous technology but the dialkyl polysulfides would not be removed. These are removed in the present invention in the chlorine step. Upon chlorination to remove organic polysulfides, reduction in the amount of dihydrocarbylchlorophosphate in the product is desired. The chlorine-treated product is contacted in the quenching zone with an aqueous solution of a reducing agent, preferably an alkali metal sulfite or bisulfite. In such case, the quenching zone in the continuous process should be designed and operated to provide a residence time for the contents thereof sufficient to effect the desired decrease in dihydrocarbylchlorophosphate impurity content. Typically, residence times for the treatment with the aqueous reducing agent solution are within the range of about 5 and about 10 minutes. However longer periods may be used whenever deemed necessary or desirable.

The following Examples illustrate practice of the process of this invention, but are not intended to limit the scope of this invention.

The analyses in the Examples were carried out using a capillary gas chromatographic procedure for the determination of diethylchlorothiophosphate (DECTP) and its minor impurities. In this procedure, DECTP (2 uL) is injected without solvent dilution into a Hewlett-Packard Model 5890 gas chromatograph equipped with a temperature programmer, a 25 m×0.32 mm I.D. fused silica capillary column (Quadrex 5μ, crosslinked SE-54), and a low volume thermal conductivity detector. The injector temperature was held at 150° C. and the detector was kept at 275° C. Helium carrier gas was used at a flow rate of 5 mL/min through the column with a splitter vent flow rate of 100 mL/min. The oven was temperature programmed linearly: 100° C. initially, held 4 minutes and increased at a rate of 15° C./minute to 160° C. The retention times of DECTP, DECP, and $Et_2S_3$ were 10.1, 9.0, and 10.7 minutes, respectively. The peaks of all components were integrated with a digital integrator and calculated as normalized area percentages.

Example 1 illustrates conduct of the chlorination step in a closed system.

EXAMPLE 1

A reactor system was constructed as shcematically depicted in FIG. 1. The system was composed of a 400 mL shielded gas bottle 10 which served as the reaction vessel, and a 90 mL jacketed gas bottle 20 serving as a feed vessel. These were connected with ⅛" Teflon® fluoropolymer tubing 30 interspersed with valves 35, 35, a tee 40, and a pressure gauge 50. In addition, a pressure relief valve 55 was connected to tubing 30. The reaction vessel was filled with 200 mL DECTP and the preevacuated feed vessel was filled with chlorine to an initial pressure of 36.5 psig. Addition of chlorine into the DECTP was instantaneous via a stopcock and the final gauge pressure was 0 psig, a pressure decrease which occurred almost immediately with no hint of increasing pressure during the chlorine addition to the DECTP. A yellow-colored organic solution was observed, along with very slight gaseous evolution. The initial temperature was approximately 25° C. A portion of the reaction mass was processed by addition of 6 mL of the chlorine-treated DECTP into 10 mL 0.5 N NaOH, dried over 5 A molecular sieves, and analyzed by gas chromatography using a thermal conductivity detector according to the procedure described above. The initial level of diethyltrisulfide ($Et_2S_3$) in the starting DECTP was 0.13% and after the reaction described, no $Et_2S_3$ was detected. The detection limit is estimated to be 0.02 GC area % $Et_2S_3$.

Examples 2 and 3 illustrate conduct of the chlorination step as a batch operation at atmospheric pressure in a non-enclosed system.

EXAMPLE 2

DECTP (200 mL) was added into a 500 mL three-necked round bottomed flask equipped with a stirrer and maintained under a nitrogen atmosphere. Chlorine (0.70 g) was added through a ⅛" diptube at a level extending 0.5 to 1.0 inch (ca. 1.27 to 2.54 cm) beneath the liquid surface. After 18 seconds of reaction time at ambient temperature, a 4 mL aliquot of the organic was quenched into 10 mL 2.5% NaOH, and the organic portion was separated, dried over 5 A molecular sieves, and analyzed by GC as described above. The level of diethyltrisulfide was decreased from an initial level of 0.14% in the starting DECTP to <0.02% in the reaction product.

EXAMPLE 3

A 500 mL three-necked round bottomed flask was equipped with a stirrer and a dip tube. While maintaining the system under a nitrogen atmosphere, chlorine (0.57 g) was sparged from the dip tube into DECTP (200 mL) in the flask at ambient temperature while stirring the contents of the flask. After such addition, a 4 mL portion of the organic phase was added into 10 mL of a 2% aqueous NaOH solution, and then the organic portion was separated and dried over 5 A molecular sieves, and analyzed by GC as described above. GC analysis of the starting DECTP showed 97.69% DECTP, 0.65% ethyldichlorophosphate (EDCP), and 0.12% $Et_2S_3$. GC analysis of the chlorine-treated product showed 97.83% DECTP, 0.58% EDCP, and no $Et_2S_3$ was detected (<0.02%).

Example 4 illustrates a batch operation using chlorine diluted with an inert gas.

EXAMPLE 4

A 500 mL three-necked round bottomed flask was equipped with stirrer and a dip tube. While maintaining the system under a nitrogen atmosphere, a mixture of chlorine (1.1 g) and nitrogen was sparged at a rate of 20 mL/min from the dip tube into DECTP (200 mL) in the flask at ambient temperature while stirring the contents of the flask. After such addition, a 4 mL portion of the organic phase was added into 10 mL 2% aqueous NaOH solution, and then the organic portion was separated and dried over 5 A molecular sieves, and analyzed by GC as described above. The starting DECTP used in this operation was another portion of the same crude product as used in Example 3, and thus contained 97.69% DECTP, 0.65% EDCP, and 0.12% Et2S3. GC analysis of the chlorine-treated product from this operation showed 97.52% DECTP, 0.53% EDCP, and 0.02% $Et_2S_3$.

Example 5 illustrates operation of the process as a continuous process.

EXAMPLE 5

A stream of crude DECTP and a metered trace level feed of chlorine were brought into homogeneous contact at ambient temperature in an inline pipe mixer. The initial DECTP contained from 0.05 to 0.35% diethyltrisulfide as determined by the above GC procedure. The DECTP flow rate was in the range of 3000 to 4000 lb/hr (ca. 1360 to 1820 kg/hr), and the chlorine was fed at the rate of 2 to 12 lb/hr (ca. 1 to 6 kg/hr). The excess chlorine was neutralized by co-feeding a 15 wt % aqueous $Na_2SO_3$ solution at the rate of 10 to 45 g/hr into the chlorine-treated DECTP down stream of the pipe mixer. The flowing reaction mixture was then passed into a 100-gallon stirred reactor, then to a phase separation unit where the organic layer was removed and dried. Analysis of the purified DECTP product from this operation using the above GC procedure showed the product to contain from 0 to 0.02% of the trisulfide impurity.

What is claimed is:

1. A process of upgrading a crude dihydrocarbylchlorothiophosphate product which contains as a contaminant at least one dihydrocarbylpolysulfide and/or at least one dihydrocarbylchlorophosphate and wherein the hydrocarbyl groups of said product and said contaminant are free of non-benzenoid unsaturation, which process comprises (a) contacting the crude product with elemental chlorine, (b) mixing water or an alkaline aqueous solution with the resultant product mixture, and (c) separating the resultant aqueous and organic phases from each other.

2. A process according to claim 1 wherein said crude dihydrocarbylchlorothiophosphate product is a distilled dihydrocarbylchlorothiophosphate product containing said contaminant.

3. A process according to claim 1 wherein said crude dihydrocarbylchlorothiophosphate product is a crude dialkylchlorothiophosphate product and said contaminant is (i) a dialkyltrisulfide or (ii) a dialkyltrisulfide and a dialkylchlorophosphate, and wherein the alkyl groups of the crude dialkylchlorothiophosphate product and the alkyl groups of (i) or (ii), as the case may be, each contain about 8 carbon atoms or less.

4. A process according to claim 3 wherein said crude dialkylchlorothiophosphate product is a distilled product containing said contaminant.

5. A process according to claim 3 wherein said crude dialkylchlorothiophosphate product is a crude diethylchlorothiophosphate product and said contaminant is (i) diethyltrisulfide or (ii) diethyltrisulfide and diethylchlorophosphate.

6. A process according to claim 5 wherein said crude diethylchlorothiophosphate product is a distilled product containing said contaminant.

7. A process according to claim 1 wherein said crude dihydrocarbylchlorothiophosphate product is at least contaminated with a dihydrocarbylpolysulfide and a dihydrocarbylchlorophosphate, and wherein pursuant to (b) an alkaline aqueous solution is mixed with the resultant product mixture.

8. A process according to claim 7 wherein said alkaline aqueous solution is a solution of a water-soluble sulfite or bisulfite salt.

9. A process according to claim 8 wherein said alkaline aqueous solution is an alkaline aqueous solution of an alkali metal sulfite or bisulfite.

10. A process according to any of claims 1–9 wherein the process is conducted as a continuous process.

11. A process which comprises (a) mixing together (i) elemental chlorine and (ii) a crude dihydrocarbylchlorothiophosphate product which contains as a contaminant at least one dihydrocarbylpolysulfide and/or at least one dihydrocarbylchlorophosphate and wherein the hydrocarbyl groups of said product and said contaminant are free of non-benzenoid unsaturation; (b) mixing together the resultant chlorine-treated product and an alkaline aqueous solution; and (c) separating the resultant aqueous and organic phases from each other.

12. A process according to claim 11 wherein said crude dihydrocarbylchlorothiophosphate product is contaminated at least with a dihydrocarbyltrisulfide and a dihydrocarbylchlorophosphate, and wherein said alkaline aqueous solution is an alkaline aqueous solution of a water-soluble sulfite or bisulfite salt.

13. A process according to claim 12 wherein said alkaline aqueous solution is an aqueous solution of an alkali metal sulfite or bisulfite.

14. A process according to claim 11 wherein said crude dihydrocarbylchlorothiophosphate product is a crude diethylchlorothiophosphate product contaminated at least with (i) diethyltrisulfide or (ii) diethyltrisulfide and diethylchlorophosphate.

15. A process according to claim 14 wherein said alkaline aqueous solution is an alkaline aqueous solution of a water-soluble sulfite or bisulfite salt.

16. A process according to claim 15 wherein said alkaline aqueous solution is an aqueous solution of an alkali metal sulfite or bisulfite.

17. A process according to any of claims 11–16 wherein the crude product is a distilled product containing the contaminant.

18. A process of reducing or eliminating the diethyltrisulfide content of a crude diethylchlorothiophosphate product which is contaminated at least with diethyltrisulfide, which process comprises (a) mixing and reacting gaseous chlorine with the crude product; (b) mixing water or an alkaline aqueous solution with product from (a); and (c) separating the resultant aqueous and organic phases from each other.

19. A process according to claim 18 wherein the gaseous chlorine is diluted with at least one inert gas.

20. A process according to claim 18 wherein said crude diethylchlorothiophosphate product is a distilled diethylchlorothiophosphate product contaminated at least with diethyltrisulfide.

21. A process according to claim 20 wherein the gaseous chlorine is diluted with at least one inert gas.

22. A process according to any of claims 18–21 wherein the crude product is also contaminated with diethylchlorophosphate; and wherein pursuant to (b) an alkaline aqueous solution is mixed with product from (a).

23. A process according to any of claims 18–21 wherein the crude product is also contaminated with diethylchlorophosphate; and wherein pursuant to (b) an aqueous alkaline sulfite or bisulfite solution is mixed with product from (a).

24. A process which comprises:
  a) continuously feeding a crude dihydrocarbylchlorothiophosphate product contaminated with at least one dihydrocarbylpolysulfide and/or at least one dihydrocarbylchlorophosphate into a reaction zone while concurrently feeding chlorine into the reaction zone such that the chlorine and the crude product come into intimate contact with each other;
  b) concurrently withdrawing chlorine-contacted contents from the reaction zone at a volumetric rate substantially equivalent to the volumetric rate at which the feeds are being introduced into the reaction zone;
  c) continuously feeding the contents withdrawn from the reaction zone into a quenching zone, and mixing such contents therein with an aqueous alkaline solution to at least quench any excess chlorine and extract from the dihydrocarbylchlorothiophosphate product water-soluble impurities present therein; and
  d) separating the resultant aqueous and organic product phases from each other.

25. A process according to claim 24 wherein in a) the chlorine is fed as gaseous chlorine, and wherein in c) the aqueous alkaline solution used is an aqueous alkaline sulfite or bisulfite solution.

26. A process according to claim 24 wherein said crude dihydrocarbylchlorothiophosphate product is a distilled diethylchlorothiophosphate product contaminated at least with diethyltrisulfide and diethylchlorophosphate.

27. A process according to claim 26 wherein in a) the chlorine is fed as gaseous chlorine, and wherein in c) the aqueous alkaline solution used is an aqueous alkaline sulfite or bisulfite solution.

* * * * *